United States Patent [19]

Harwin et al.

[11] Patent Number: 5,618,314
[45] Date of Patent: Apr. 8, 1997

[54] SUTURE ANCHOR DEVICE

[76] Inventors: Steven F. Harwin, 1050 Park Ave., New York, N.Y. 10021; Anh Le, 118 Wainwright Dr., Matawan, N.J. 07747; Izi Bruker, 18 Pleasant View Way, Flemington, N.J. 08822; Brian Luscombe, 43 Eton Way, Somerset, N.J. 08873; Dennis D. Jamiolkowski, 20 Fawnridge Dr., Long Valley, N.J. 07853; Mark Cofone, 24 Pebble Ct., Holland, Pa. 18966; John DiGiovanni, 5 Winston Dr., Woodbridge, N.J. 07095

[21] Appl. No.: 166,493

[22] Filed: Dec. 13, 1993

[51] Int. Cl.⁶ ............................................. A61B 17/04
[52] U.S. Cl. ........................ 606/232; 606/76; 606/72; 606/74; 606/73
[58] Field of Search ............................ 606/232, 104, 606/72, 74, 75

[56] References Cited

U.S. PATENT DOCUMENTS

| D. 331,463 | 12/1992 | Rosenberg et al. . | |
|---|---|---|---|
| D. 331,626 | 12/1992 | Hayhurst et al. . | |
| 4,011,602 | 3/1977 | Rybichie et al. . | |
| 4,013,071 | 3/1977 | Rosenberg . | |
| 4,632,100 | 12/1986 | Somers et al. . | |
| 4,721,103 | 1/1988 | Freedland . | |
| 4,738,255 | 4/1988 | Goble et al. . | |
| 4,759,765 | 7/1988 | Van Kampen . | |
| 4,772,286 | 9/1988 | Goble et al. . | |
| 4,784,126 | 11/1988 | Hourahane . | |
| 4,828,562 | 5/1989 | Kenna . | |
| 4,834,752 | 5/1989 | Van Kempen . | |
| 4,851,005 | 7/1989 | Hunt et al. . | |
| 4,870,957 | 10/1989 | Goble et al. . | |
| 4,875,148 | 1/1990 | Bays et al. . | |
| 4,898,156 | 2/1990 | Gatturna et al. . | |
| 4,924,865 | 5/1990 | Bays et al. . | |
| 4,927,421 | 5/1990 | Goble . | |
| 4,976,715 | 12/1990 | Bays et al. . | |
| 5,002,550 | 3/1991 | Li . | |
| 5,013,316 | 5/1991 | Goble . | |
| 5,037,422 | 8/1991 | Hayhurst . | |
| 5,041,129 | 8/1991 | Hayhurst et al. . | |
| 5,064,425 | 11/1991 | Branemark et al. . | |
| 5,084,050 | 1/1992 | Draenert . | |
| 5,102,414 | 4/1992 | Kirsch . | |
| 5,102,421 | 4/1992 | Anspach, Jr. | 606/232 |
| 5,116,337 | 5/1992 | Johnson . | |
| 5,129,906 | 7/1992 | Ross et al. . | |
| 5,141,520 | 8/1992 | Goble et al. | 606/232 |
| 5,147,362 | 9/1992 | Goble . | |
| 5,152,790 | 10/1992 | Rosenberg et al. . | |
| 5,156,616 | 10/1992 | Meadows et al. | 606/232 |
| 5,167,665 | 12/1992 | McKinney . | |
| 5,176,682 | 1/1992 | Chow . | |
| 5,192,303 | 3/1993 | Gatturna et al. . | |
| 5,203,784 | 4/1993 | Rass et al. . | |
| 5,224,946 | 7/1993 | Hayhurst et al. | 606/232 |
| 5,236,445 | 8/1993 | Hayhurst et al. . | |
| 5,258,016 | 11/1993 | DiPoto et al. | 606/232 |
| 5,324,308 | 6/1993 | Pierce | 606/232 |

FOREIGN PATENT DOCUMENTS

| 0464479 | 1/1992 | European Pat. Off. . |
|---|---|---|
| 0464480 | 1/1992 | European Pat. Off. . |
| 0502509 | 9/1992 | European Pat. Off. . |
| 0504915 | 9/1992 | European Pat. Off. . |
| WO8603666 | 7/1986 | WIPO . |
| WO8809157 | 12/1988 | WIPO . |

*Primary Examiner*—Michael Powell Buiz
*Assistant Examiner*—Mark S. Leonardo
*Attorney, Agent, or Firm*—Graham & James LLP

[57] ABSTRACT

A suture anchor having an anchor member, a central shaft and outwardly extending wing members. A suture mounting hole is provided in the suture anchor for receiving a surgical suture. The suture anchor is inserted into a bore hole in a bone as part of an orthopedic surgical procedure wherein soft tissue such as a tendon is attached to the surface of the bone. Optionally, bone tissue may be attached to the surface of the bone. The wings may have cutting edges or piercing points. The suture anchors may have screw threads on their outer surfaces.

17 Claims, 11 Drawing Sheets

SUTURE ANCHOR DEVICE

TECHNICAL FIELD

The field of art to which this invention relates is suture anchors, more specifically, suture anchors for attaching soft tissue to bone.

Background Art

As the treatment of injuries to joints and soft tissue has progressed in the orthopedic medical arts, there has been a need for medical devices which can be used to attach tendons, ligaments and other soft tissue to bone. When surgically repairing an injured joint, it is preferable to restore the joint by reattaching the damaged soft tissues rather than replacing them with an artificial material. Such restorations typically require the attachment of soft tissue such as ligaments and tendons to bone.

An increase in the incidence of injuries to joints involving soft tissue has been observed. This increased incidence may be due, at least in part, to an increase in participation by the public in various physical activities such as sports and other recreational activities. These types of activities may increase the loads and stress placed upon joints, sometimes resulting in joint injuries with corresponding damage to associated soft tissue. In 1991, for example, there were approximately 560,000 surgical procedures performed in the United States in which soft tissue was attached to a bone in various joints including the shoulder, hip and knee.

One conventional orthopedic procedure for reattaching soft tissue to bone is performed by initially drilling holes or tunnels at predetermined locations through a bone in the vicinity of a joint. Then, the surgeon approximates soft tissue to the surface of the bone using sutures threaded through these holes or tunnels. This method, although effective, is a time consuming procedure resulting in the generation of numerous bone tunnels. The bone tunnels, which are open to various body fluids and infectious agents, may become infected or break. Other known complications may arise including a longer bone-healing period, etc. A known complication of drilling tunnels across bone is that nerves and other soft tissue structures may be injured by the drill bit or orthopaedic pin as it exits the far side of the bone. Also, it may be anatomically impossible or at least very difficult to reach and/or secure a suture/wire that has been passed through a tunnel. When securing the suture or wire on the far side of the bone, nerves and soft tissues can become entrapped and damaged.

In order to overcome some of the problems associated with the use of the conventional bone tunnel procedures, suture anchors have been developed and are frequently used to attach soft tissue to bone or bone to bone. A suture anchor is an orthopedic, medical device which is typically implanted into a cavity drilled into a bone. These devices are also referred to as bone anchors. The cavity is typically referred to as a bore hole and usually does not extend through the bone. This type of bore hole is typically referred to as a "blind hole". The bore hole is typically drilled through the outer cortex layer of the bone and into the inner cancellous layer. The suture anchor may be engaged in the bore hole by a variety of mechanisms including friction fit, barbs which are forced into the cancellous layer of bone, etc. Suture anchors are known to have many advantages including reduced bone trauma, simplified application procedures, and decreased likelihood of suture failure. Suture anchors may be used in the Bankart shoulder reconstruction for repairing the glenohumeral ligament and may also be used in surgical procedures involving rotator cuff repair, ankle and wrist repair, bladder neck suspension, and hip replacement.

Suture anchors typically have a hole or opening for receiving a suture. The suture extends out from the bore hole and is used to attach soft tissue. The suture anchors presently described in the art may be made of absorbable materials which absorb over time, or they may be made from various non-absorbable, biocompatible materials. Although most suture anchors described in the art are made from non-absorbable materials, the use of absorbable suture anchors may result in fewer complications since the suture anchor is absorbed and replaced by bone over time. In addition, the use of absorbable suture anchors may reduce the likelihood of damage to local joints caused by anchor migration. Moreover, when an absorbable suture anchor is fully absorbed it will no longer be present as a foreign body.

Although suture anchors for attaching soft tissue to bone are available for use by the orthopedic surgeon, there is a constant need in this art for novel suture anchors having improved performance characteristics, such as ease of insertion and greater resistance to "pull-out".

Disclosure of the Invention

Therefore, it is an object of the present invention to provide a suture anchor which is mechanically stable when implanted in bone and which is simple to apply.

It is a further object of the present invention to provide a suture anchor which is easy to manufacture.

It is a further object of the present invention to provide an absorbable suture anchor.

Accordingly, a suture anchor device is disclosed. The suture anchor has an anchor member which has a distal end, a proximal end and, preferably, a circular cross-section, although other geometric cross-sections may be used. The cross-section may vary along the length of the anchor member. A shaft having a distal end, a proximal end, and a longitudinal axis extends from the proximal end of the anchor member. Optional grasping means extend from the proximal end of the shaft. The grasping means are used for inserting and manipulating the suture anchor device. At least two wing members extend proximally and radially from the proximal end of the anchor member. An optional blunted tip extends distally from the distal end of the anchor member. The wing members have a fixed distal end and a proximal free end and opposed sides. The wing members may also have a cutting means extending from at least one side for cutting into bone when the suture anchor device is rotated in a bore hole in bone. A suture retaining means is mounted to the shaft, preferably to the proximal end of the shaft.

Yet another aspect of the present invention is a suture anchor device which is further secured in the bone by a penetration action. The suture anchor device has an anchor member which has a distal end, a proximal end and, preferably, a circular cross-section, although other geometric cross-sections may be used. The cross-section may vary along the length of the anchor member. A shaft having a distal end, a proximal end, and a longitudinal axis extends from the proximal end of the anchor member. Optional grasping means extend from the proximal end of the shaft. The grasping means are used for inserting and manipulating the suture anchor device. At least two wing members extend proximally and radially from the proximal end of the anchor member. An optional blunted tip extends distally from the distal end of the anchor member. The wing members have a fixed distal end and a proximal free end and opposed sides. The wing members also have a pointed section extending from each proximal end for penetrating into bone when the suture anchor device is tugged upon after insertion into a bore hole. The pointed sections of the wings can be made to penetrate the bone by action of an applier or alternately or in combination with the forces that can be exerted by optional sutures attached to the anchor. A suture retaining means is mounted to the shaft, preferably to the distal end of the shaft.

Yet another aspect of the present invention is an anchor member for a suture. The anchor member has an elongated body member having a distal end and a proximal end. A plurality of wing members, having a normally open position, extend proximally and radially outward. Each wing member has a distal end fixed to said body member and a proximal free end. The wing members are operable, after being deflected inwardly to a closed position, to automatically return to the normally open position. A suture is mounted to the elongated body member.

Yet another aspect of the present invention is any of the above-described suture anchors additionally having a screw thread extending from the outer surface of the anchor member.

An additional aspect of the present invention is an apparatus for inserting a suture anchor device into a bone bore hole, the apparatus comprising a tubular member having a passage therethrough and an open proximal end and an open distal end, a shaft having a distal end and a proximal end slidably mounted in the tubular member, actuation means mounted to the proximal end of the shaft for sliding the shaft between two positions within the tubular members, and operator means mounted to the distal end of the shaft for receiving and engaging a suture anchor device when the shaft is in one of the positions and for releasing the suture anchor device when the shaft is in the other of the positions.

Still yet another aspect of the present invention is a method of implanting any of the above-described suture anchor devices in bone.

The foregoing and other features and advantages of the present invention will become more apparent from the following description and accompanying drawings.

BEST MODE FOR CARRYING OUT THE INVENTION

The suture anchor device 5 of the present invention is seen in FIGS. 1–7. Referring to FIGS. 1–6, the suture anchor device 5 is seen to have an anchor member 10 having distal end 14 and proximal end 12. Anchor member 10 preferably has a circular cross-section which may vary in diameter along its longitudinal axis. The member 10 may have other geometric cross-sections including square, rectangular, triangular, polyhedral, elliptical, etc. A central shaft 20 having proximal end 22 and distal end 24 extends from the proximal end 12 of anchor member 10. The shaft 20 is seen to have longitudinal axis 25. The shaft 20 has suture hole 30 extending therethrough transverse to longitudinal axis 25. Suture hole 30 is preferably positioned toward the proximal end 22 of shaft 20. Although not preferred, suture hole 30 may also extend through member 10 rather than shaft 20. The suture hole 30 is preferably circular in configuration but may have other geometric configurations. Extending from the distal end 14 of anchor member 10 is blunt distal nose section 40. If desired, distal nose 40 may be tapered or pointed. Optional grasping member 50 is seen to extend proximally from the proximal end 22 of shaft 20.

Extending from the proximal end 12 of anchor member 10 are the wing members 60. The wing members 60 are seen to extend proximally and radially outward from proximal end 12. The wing members 60 are seen to have fixed distal end 62 and free proximal end 64 as well as opposed sides 68 and 69. The wing members 60 are separated from each other by slots 80. The wing members 60 are also seen to have cutting edges 70 extending from the side 68 of each wing member 60. The cutting edges 70 are formed by increasing the thickness of one side of the wing members 60 as measured radially. In the present embodiment, side 68 of wing members 60 is thicker than side 69 as measured radially, thereby forming cutting edge 70.

In an alternate embodiment (not shown), both side 68 and side 69 may have a cutting edge 70. In such an embodiment, both side 68 and side 69 would have a greater thickness measured radially than the thickness of the medial portion of wing member 60.

Figure 1:
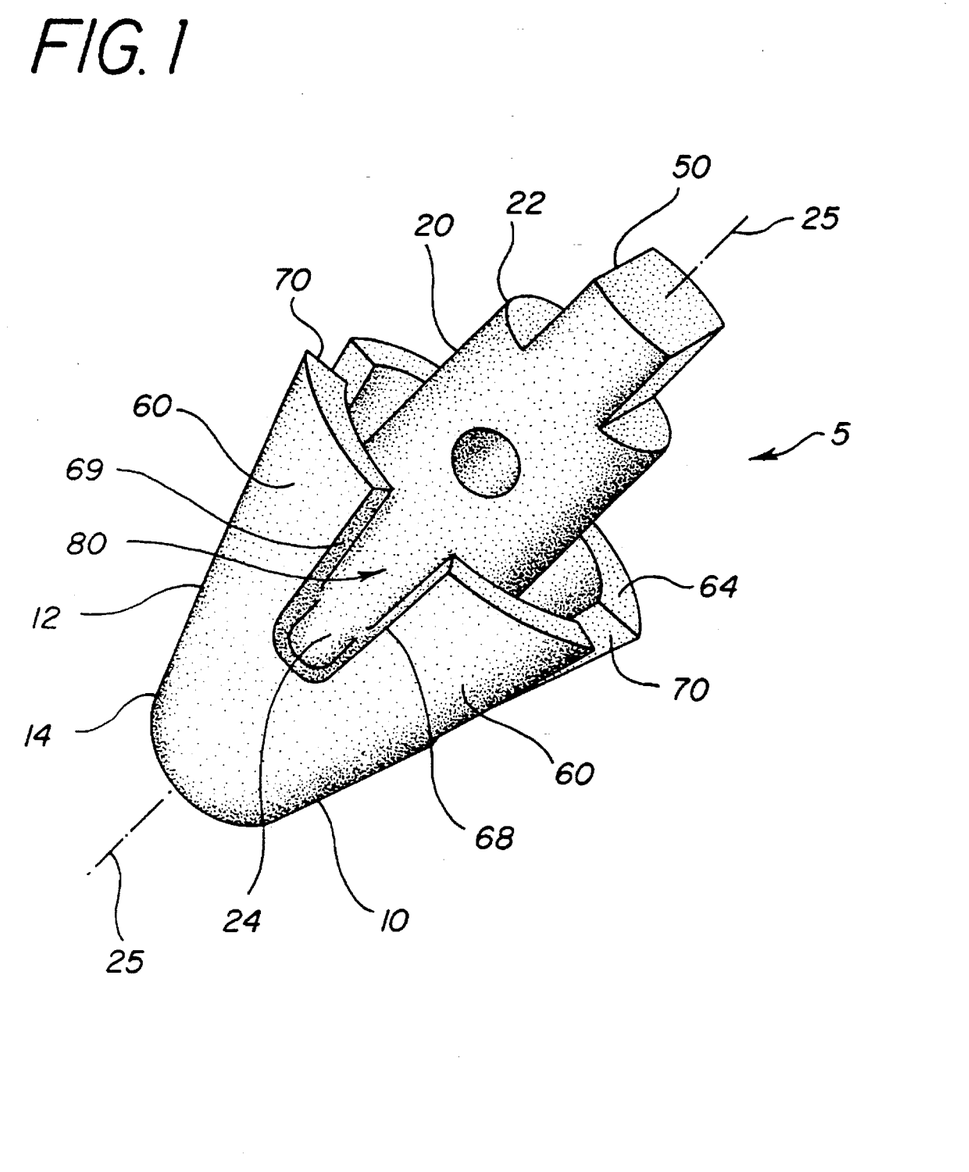
FIG. 1 is a perspective view of a suture anchor of the present invention having wing members with cutting edges.
Figure 2:
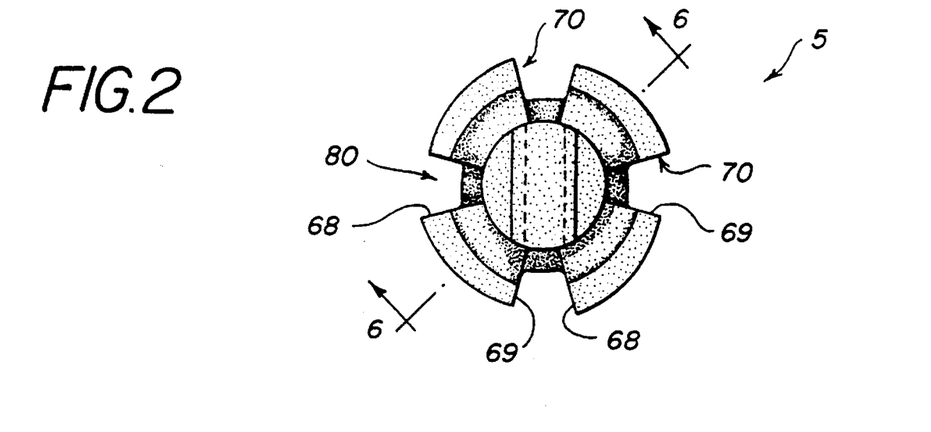
FIG. 2 is a top view of the suture anchor of FIG. 1.
Figure 3:
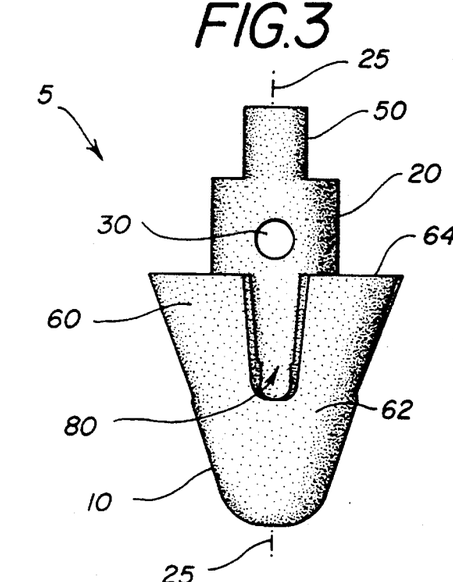
FIG. 3 is a side view of the suture anchor of FIG. 1.
Figure 4:
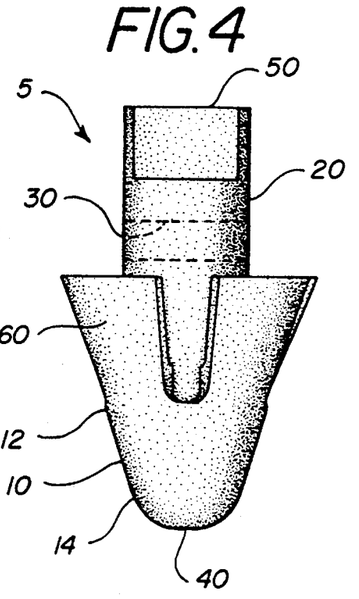
FIG. 4 is a side view of the suture anchor of FIG. 3 rotated 90°.
Figure 5:
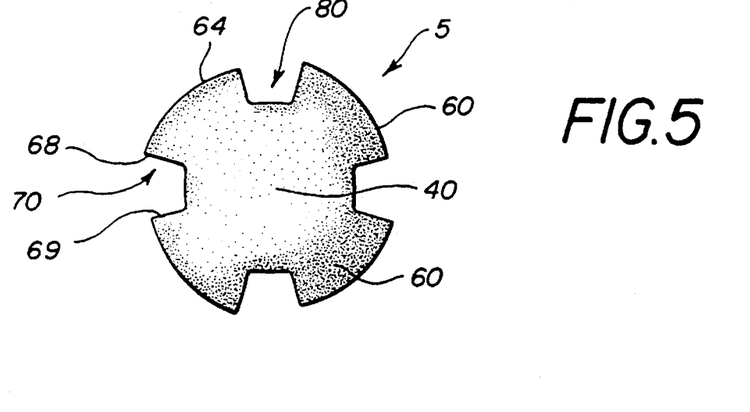
FIG. 5 is a bottom view of the suture anchor of FIG. 1.
Figure 6:
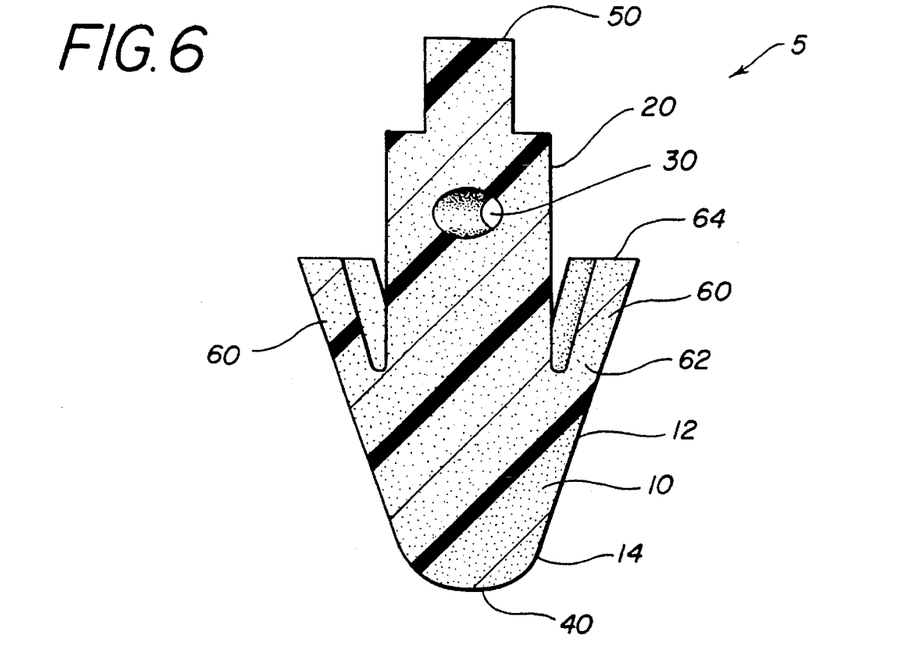
FIG. 6 is a cross-sectional view along View Line 6—6 of the suture anchor of FIG. 2.

The wing members 60 are preferably constructed to be sufficiently resilient so that they may be effectively deflected radially inward during insertion, but subsequently moved back radially outward to engage the bone and lock the device in place.

Figure 7:
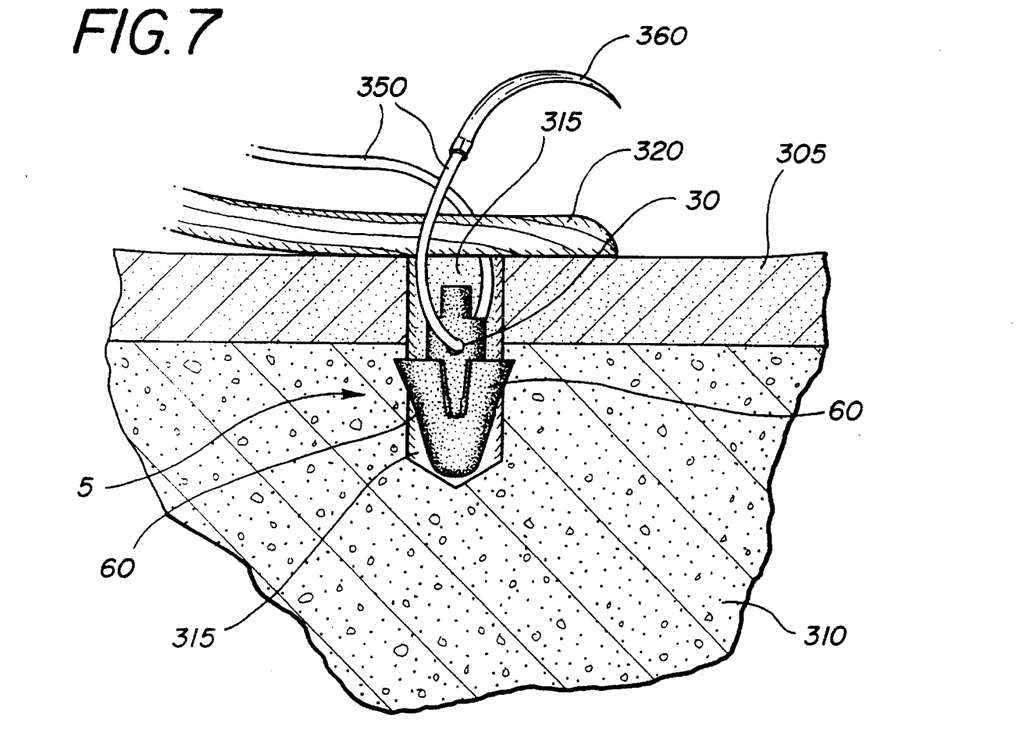
FIG. 7 is a partial cross-sectional view showing the suture anchor of FIG. 1 inserted into a bore hole drilled into a bone with a suture extended from the suture anchor through the bore hole and into a section of soft tissue which is to be attached to the bone. The wing members of the suture anchor are seen to be engaged within the cancellous layer of the bone.

The suture anchor 5 of the present invention is used by initially drilling a bore hole 315 as seen in FIG. 7 (using conventional surgical drilling instruments) of sufficient depth into a bone to effectively receive the anchor 5. The hole 315 will extend through the outer cortex layer 305 of the bone and into the underlying cancellous layer 306. The suture anchor 5 is then prepared for insertion into the hole 315 by threading suture 350 through suture hole 30, so that the anchor 5 and suture 350 and needle 360 are inserted as a unit into the hole 315. The diameter of hole 315 drilled into the bone is sized so that the wings 60 of the anchor 5 are deflected radially inwardly when the suture anchor 5 is inserted into the hole 315 using the applicator 200 (FIG. 8) or any suitable grasping instrument such as a pair of conventional surgical tweezers or a suitable surgical grasper. The suture anchor 5 is then adjusted in the hole 315 to a sufficient depth so that the suture hole 30 is positioned below (toward the cancellous bone) the upper surface 306 of the cortex of the bone and the cutting edges 70 of the wing members 60 engage the cancellous layer. Then the suture anchor 5 is rotated in the hole, preferably in a clock-wise manner, by rotating the anchor 5 with apparatus 200 or another suitable grasping instrument. The anchor 5 is rotated for a sufficient number of revolutions to allow the cutting edges 70 of the wings 60 to effectively cut into the cancellous layer surrounding the bore hole thereby allowing the deflected wings 60 to extend radially outward. The cutting action of the wings 60 increases the diameter of the hole in the bone in the cancellous layer such that at least part of the hole in the cancellous layer is of a larger diameter than the diameter of the bore hole through the cortex layer. The proximal ends 64 of the wings 60 are then sufficiently engaged in the cancellous layer of the bone to effectively prevent the anchor 5 from being pulled from the bore hole.

The amount of rotation of the anchor 5 that is required to set anchor 5 in a bone bore hole is a function of a number of factors including the nature of the material from which the anchor 5 is made and the condition of the bone. Several rotations are typical. Enlarging the diameter of the bore hole 315 can be facilitated by the inclusion of a conventional fine diamond film (not shown) on the cutting edges 70 of the wing members; this can be manufactured using conventional processes including carbon deposition.

Another embodiment of the suture anchor device of the present invention is seen in FIGS. 9–16. Referring to FIGS. 9–13, the suture anchor device 105 is seen to have an anchor member 110 having distal end 114 and proximal end 112. Anchor member 110 preferably has a circular cross-section which may vary in diameter along its longitudinal axis 125. The member 110 may have other cross-sections including square, rectangular, triangular, polyhedral, elliptical, etc. A central shaft 120 having proximal end 122 and distal end 124 extends from the proximal end 112 of anchor member 110. The shaft 120 is seen to have longitudinal axis 125. The shaft 120 has suture hole 130 extending therethrough transverse to longitudinal axis 125. The suture hole 130 is preferably circular in configuration but may have other geometric configurations. Extending from the distal end 114 of anchor member 110 is blunt distal nose section 140. Optional grasping member 150 is seen to extend proximally from the proximal end 122 of shaft 120.

Extending from the proximal end 112 of anchor member 110 are the wing members 160. The wing members 160 are seen to extend proximally and radially outward from proximal end 112. Each wing member 160 is seen to have fixed distal end 162 and free proximal end 164 as well as sides 168 and 169. The wing members 160 are separated from each other by slots 180. Each wing member 160 is seen to have extending from the distal end 164 a piercing point 170. The wing members 160 are preferably constructed to be sufficiently resilient so that they may be effectively deflected radially inward during insertion while having sufficient elasticity and recovery to assume their pre-deformed shape after insertion into a bore hole wherein the piercing points 170 are effectively driven into the cancellous bone surrounding the bore hole.

The suture anchor 105 of the present invention is used by initially drilling a bore hole 315 (FIG. 16) of sufficient depth into a bone to effectively receive the anchor 105 with the suture 350 and needle 360 attached as shown. The hole will extend through the outer cortex layer 305 of the bone and into the underlying cancellous layer 310 but preferably not through the bone. The diameter of hole drilled into the bone is sized so that the wings 160 of the anchor 105 are deflected radially inwardly when the suture anchor 105 is inserted into the hole using applicator 200 or another suitable grasping instrument. The suture anchor 105 is then adjusted in the bore hole to a sufficient depth so that the suture passage hole 130 is positioned below the upper surface 306 of the cortex of the bone (toward cancellous bone) and the cutting points 170 of the wing members 160 effectively engage the cancellous layer 310 as the wing members deflect outwardly. The anchor 105 may be tugged proximally to further engage the points 170. The points 170 of the wings 160 are then sufficiently engaged in the cancellous layer of the bone to effectively prevent the anchor 105 from being pulled from the bore hole. If desired, the anchor 105 may be rotated in the bore hole.

Figure 16:
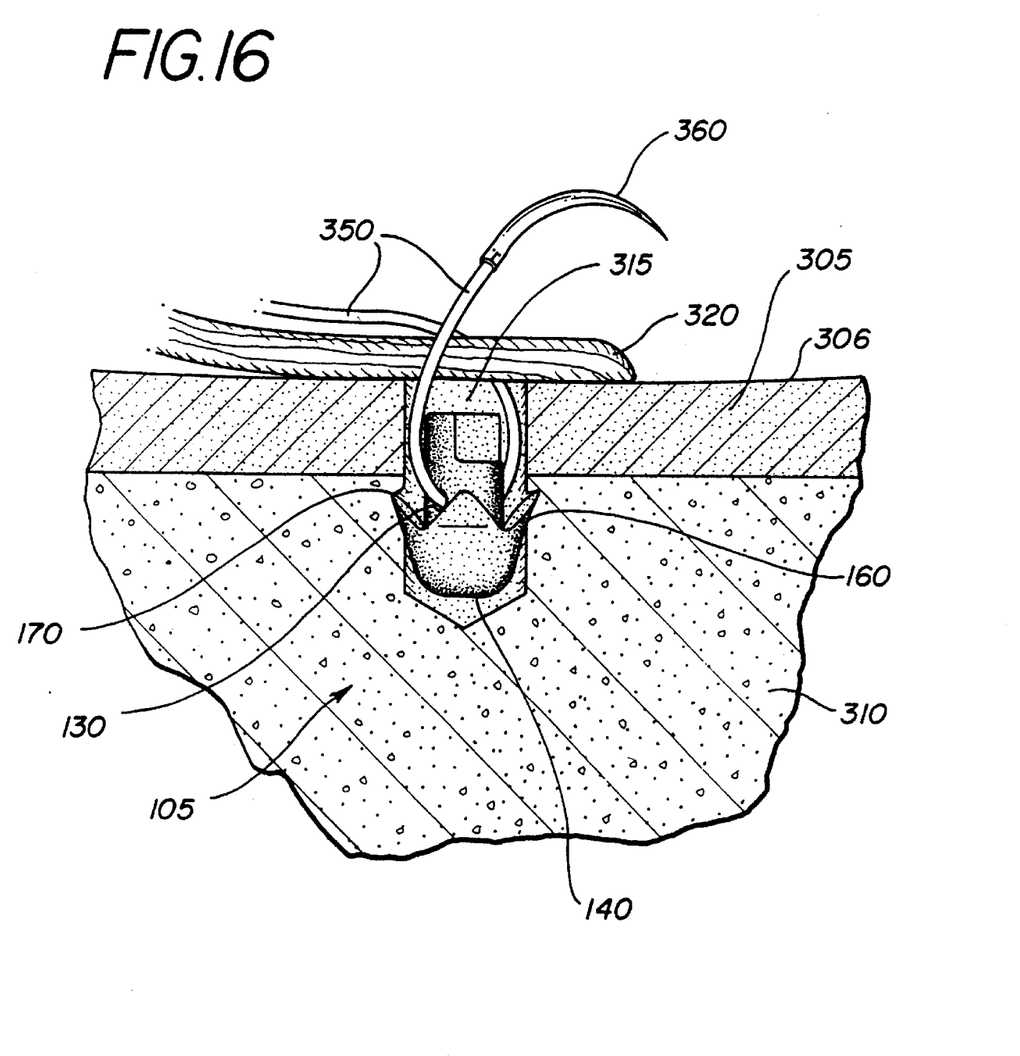
FIG. 16 is a partial cross-sectional view showing the suture anchor of FIG. 9 placed in a bore hole in a bone; the pointed, radially extending wings of the suture anchor are seen implanted in the cancellous layer of the bone. A suture is seen to extend through a suture anchor and through a section of soft tissue which is to be attached to the bone.

Referring now to FIGS. 7 and 16, after the suture anchors 5 and 105 of the present invention are implanted in bore hole 315 in bone 300, tendon 320 is secured to the surface of bone 300, specifically to the surface 306 of outer cortex 305, by inserting the needle 360 into the tendon 320 and pulling the suture 350 through the tendon 320.

Figure 17:
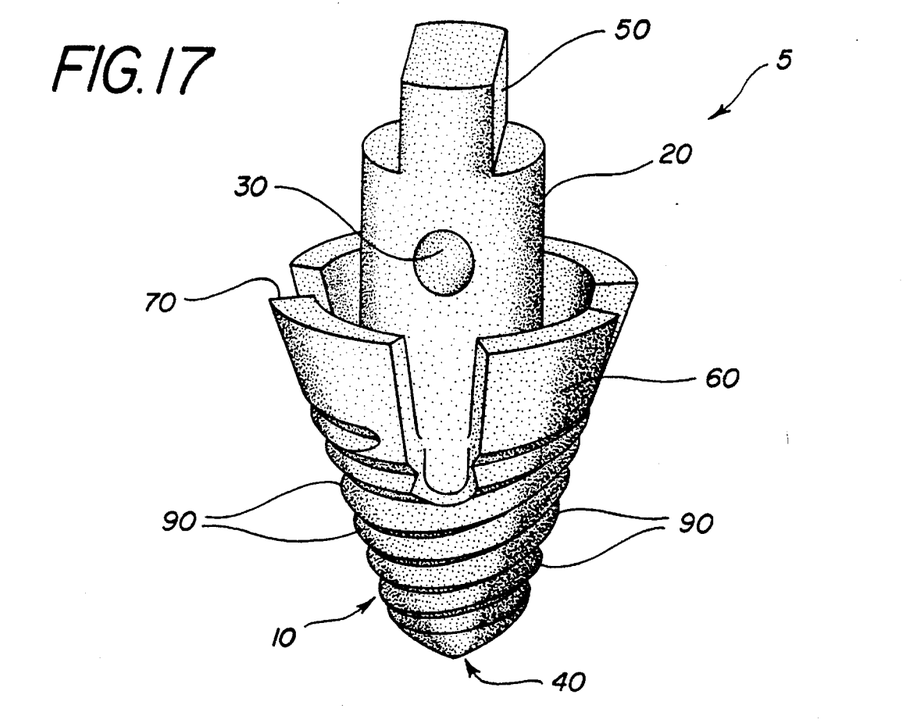
FIG. 17 is a perspective view of an alternate embodiment of a suture anchor of FIG. 1 having exterior screw threads.
Figure 18:
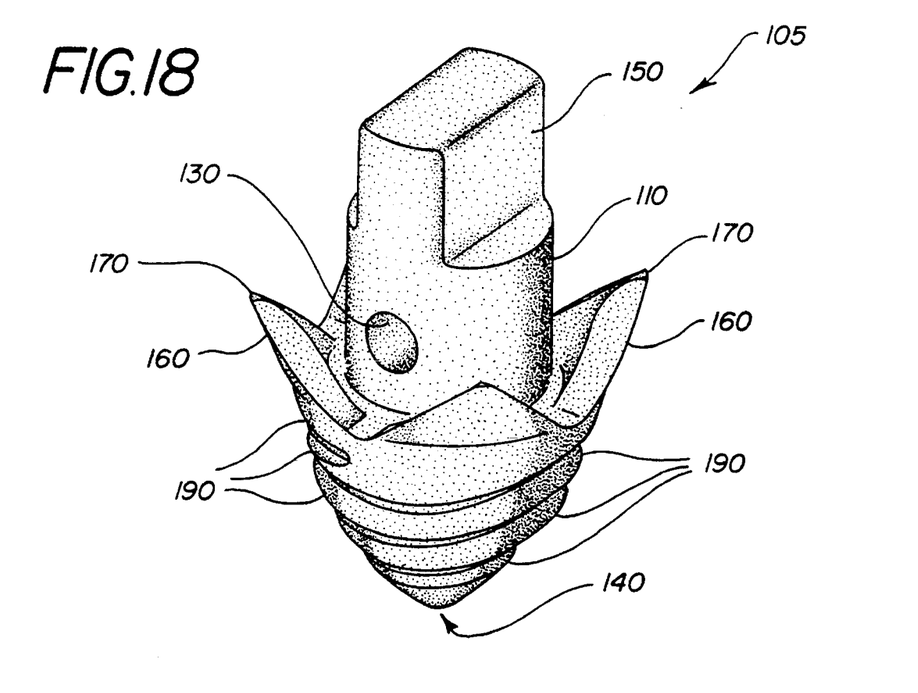
FIG. 18 is a perspective view of the suture anchor of FIG. 9 having exterior screw threads.

An alternate embodiment of the suture anchor 5 is seen in FIG. 17. The configuration of this embodiment of suture anchor 5 is similar to the configuration as previously described, however conventional screw threads 90, e.g., self-tapping screw threads, extend from the outer surfaces of the anchor member 10 and wings 60. The screw threads 90 may be present only on the anchor member 10 or may also extend to the wing members 60 as shown in FIG. 17. An alternate embodiment of the suture anchor 105 is seen in FIG. 18. The configuration of this embodiment of suture anchor 105 is similar to the configuration as previously described, however conventional screw threads 190, e.g., self-tapping screw threads, extend from the outer surface of the anchor member 110 and may extend onto wings 160. The screw threads 190 may be present only on the anchor member 110 or may also extend to the wing members 160 as shown in FIG. 17. The screw threads 90 and 190 may be molded or cut into the suture anchors 5 and 105 using conventional techniques.

Yet another embodiment of the suture anchor 5 is seen in FIGS. 19–23. The suture anchor 305 is seen to have an anchor member 310 having distal end 314 and proximal end 312. Anchor member 310 preferably has a circular cross-section which may vary in diameter along its longitudinal axis. The member 310 may have other geometric cross-sections including square, rectangular, triangular, polyhedral, elliptical, etc. A central shaft 320 having proximal end 322 and distal end 324 extends from the proximal end 312 of anchor member 310. The shaft 320 is seen to have longitudinal axis 325. The shaft 320 has suture hole 330 extending therethrough transverse to longitudinal axis 325. Suture hole 330 is preferably positioned toward the proximal end 322 of shaft 320. Although not preferred, suture hole 330 may also extend through member 310 rather than shaft 320. The suture hole 330 is preferably circular in configuration but may have other geometric configurations. Extending from the distal end 314 of anchor member 310 is blunt distal nose section 340. Optional grasping member 350 is seen to extend distally from the proximal end 322 of shaft 320.

Extending from the proximal end 312 of anchor member 310 are the wing members 360. The wing members 360 are seen to extend proximally and radially outward from distal end 324. The wing members 360 are seen to have fixed distal end 362 and free proximal end 364 as well as opposed sides 368 and 369. The wing members 360 are separated from each other by slots 380. Opposed sides 368 and 369 are seen to be of equal thickness. No cutting edge 70 such as that of anchor 5 is present along the sides of the wing members 360. Wing members 360 are sufficiently resilient such that when deflected radially inward for insertion into a bone bore hole they will effectively expand to anchor themselves in a cancellous section of bone. The anchor 305 may also be optionally rotated to assist in anchoring. Anchor 305 may also have optional distal screw threads.

Figure 19:
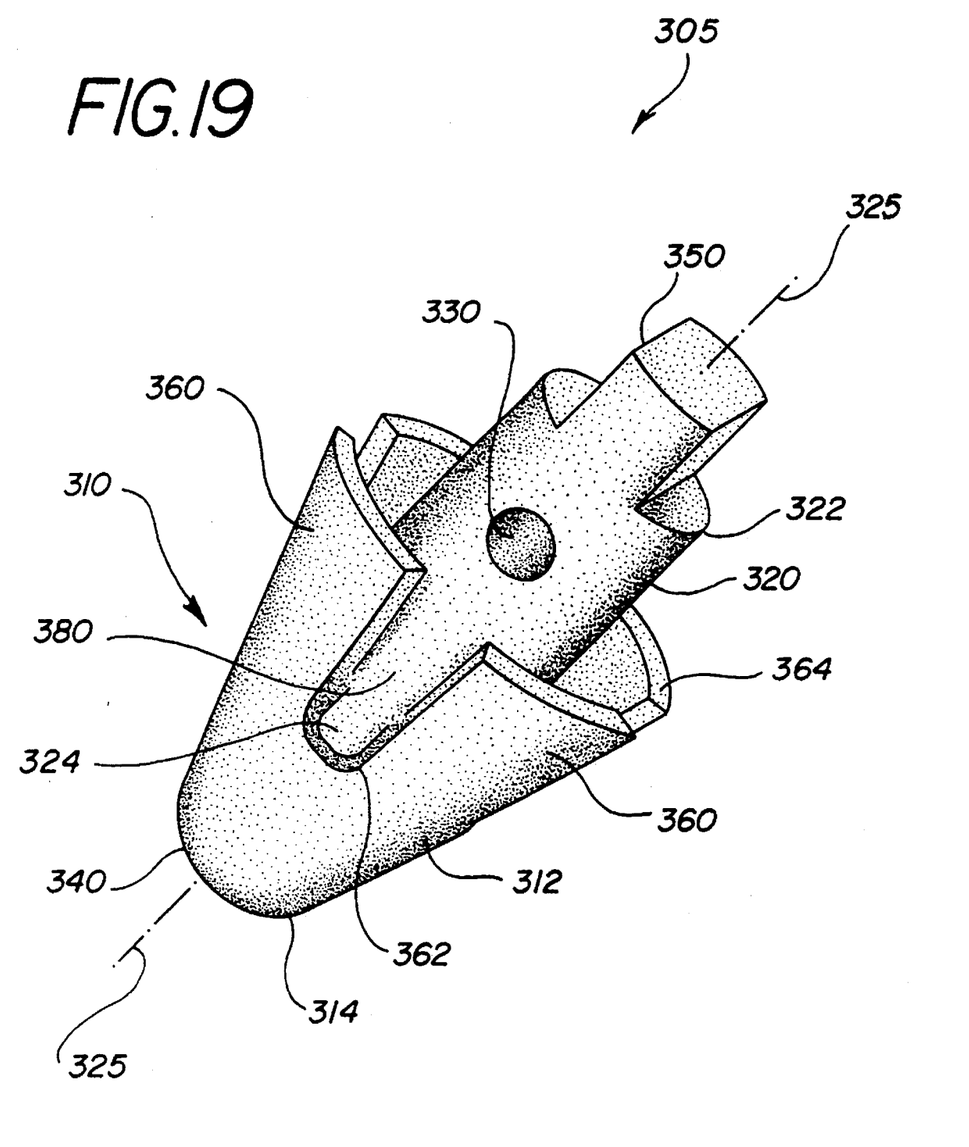
FIG. 19 is a perspective view of a suture anchor of the present invention having wing members without cutting edges.
Figure 20:
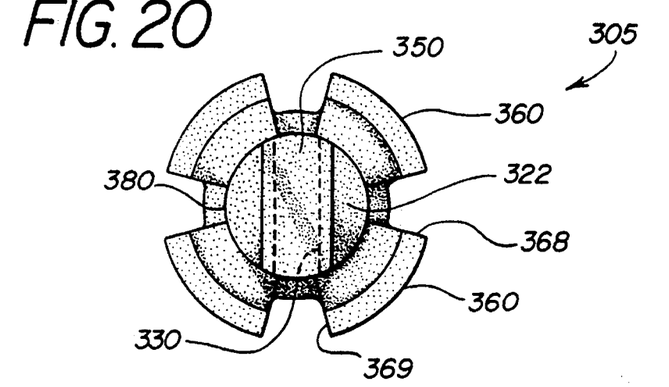
FIG. 20 is a top view of the suture anchor of FIG. 19.
Figure 21:
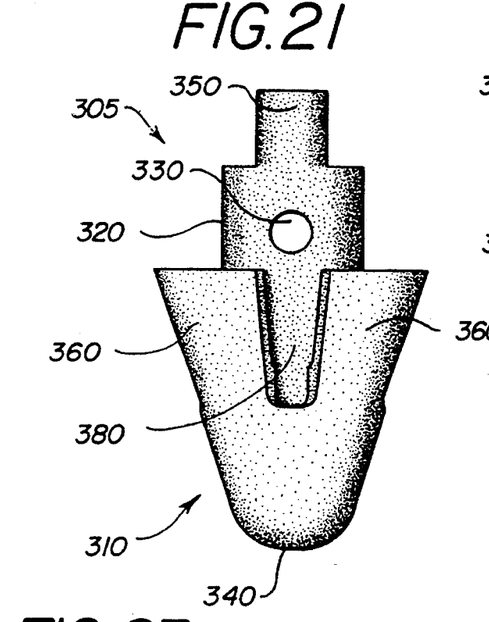
FIG. 21 is a side view of the suture anchor of FIG. 19.
Figure 22:
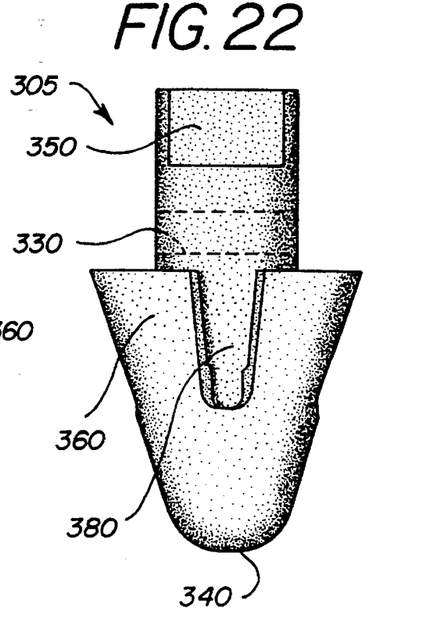
FIG. 22 is a side view of the suture anchor of FIG. 19 rotated 45°.
Figure 23:
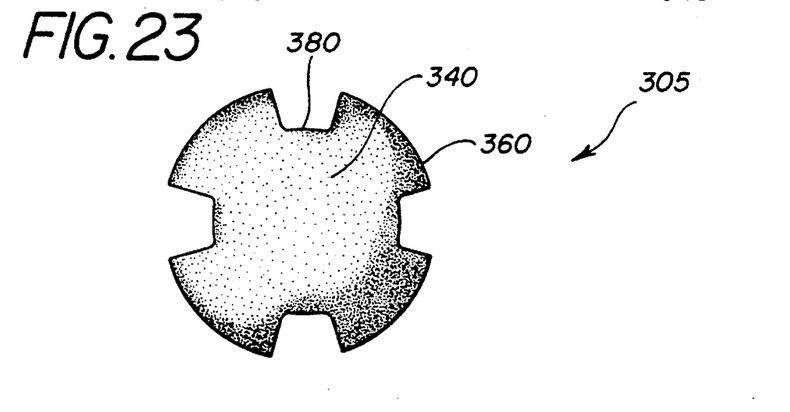
FIG. 23 is a bottom view of the suture anchor of FIG. 19.

The anchors 305 are used in a manner similar to that of anchor 105 and may be rotated in a manner similar to that of anchor 5.

Figure 8:
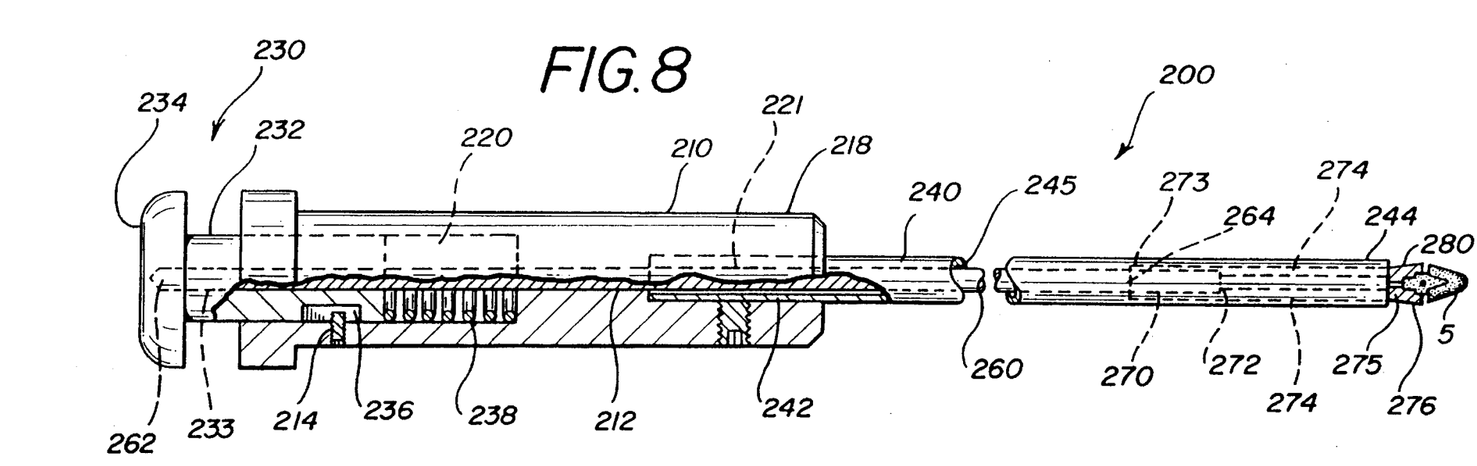
FIG. 8 is side view, having a partial cutaway, of an applicator device used to apply the suture anchors of the present invention.
Figure 8A:
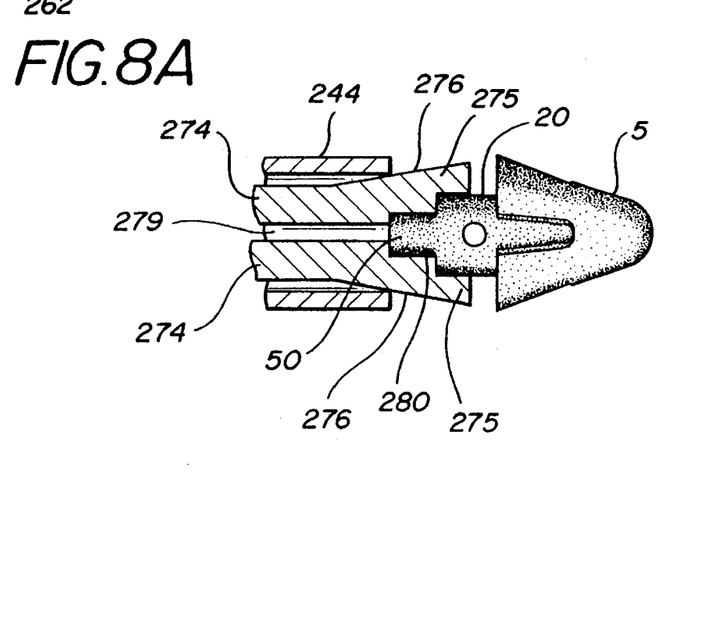
FIG. 8A is a partial cross-sectional view of the distal end of applicator device of FIG. 8 illustrating the anchor retention members.
Figure 8B:
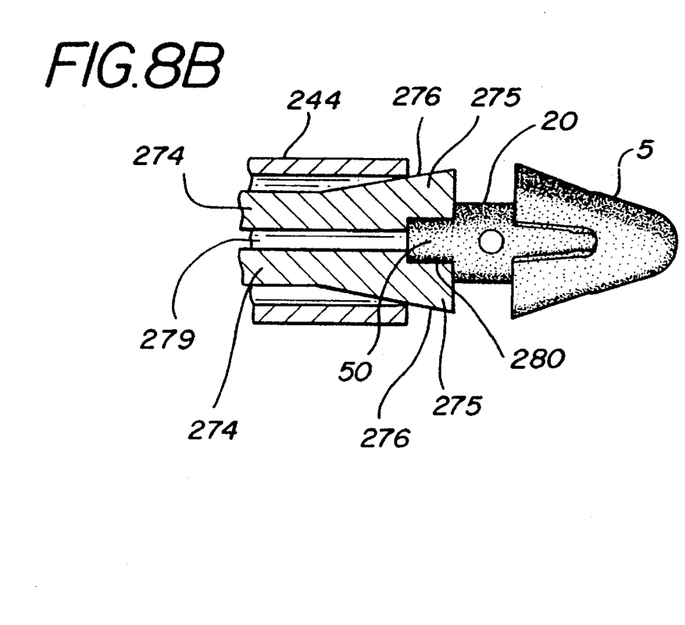
FIG. 8B is a partial cross-sectional view of the distal end of the applicator device of FIG. 8 illustrating an alternate embodiment of the anchor retention members.
Figure 9:
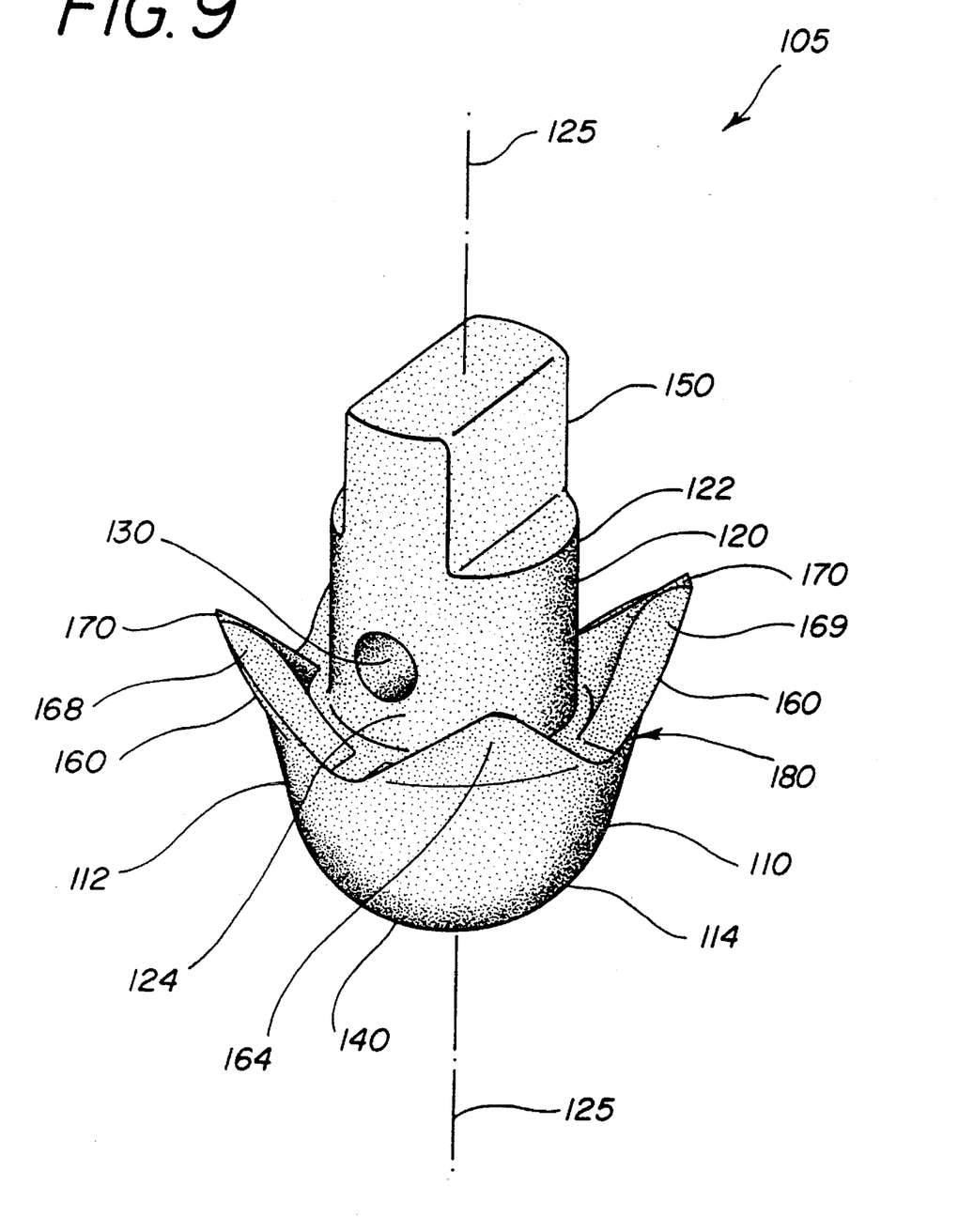
FIG. 9 is a perspective view of an alternate embodiment of a suture anchor of the present invention having proximally and radially extending wings terminating in points.
Figure 10:
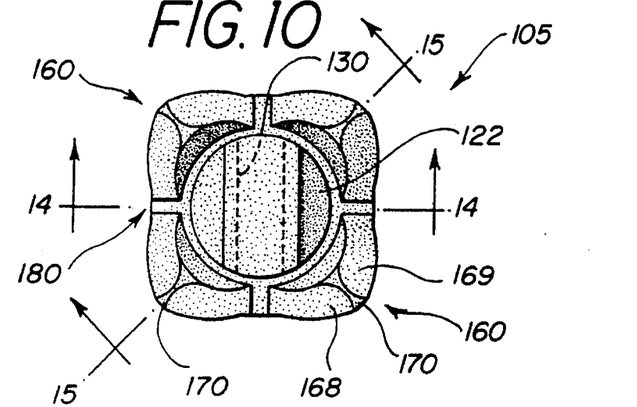
FIG. 10 is a top view of the suture anchor of FIG. 9.
Figure 11:
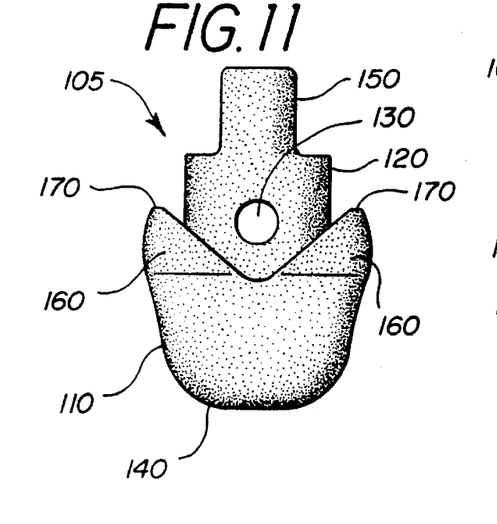
FIG. 11 is a side view of the suture anchor of FIG. 10.
Figure 12:
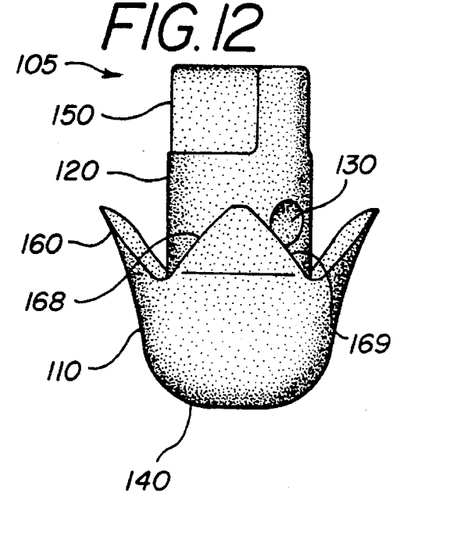
FIG. 12 is a side view of the suture anchor of FIG. 12 rotated 45°.
Figure 13:
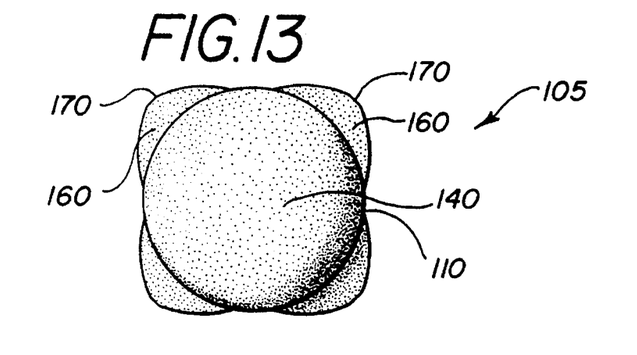
FIG. 13 is a bottom view of the suture anchor of FIG. 9.
Figure 14:
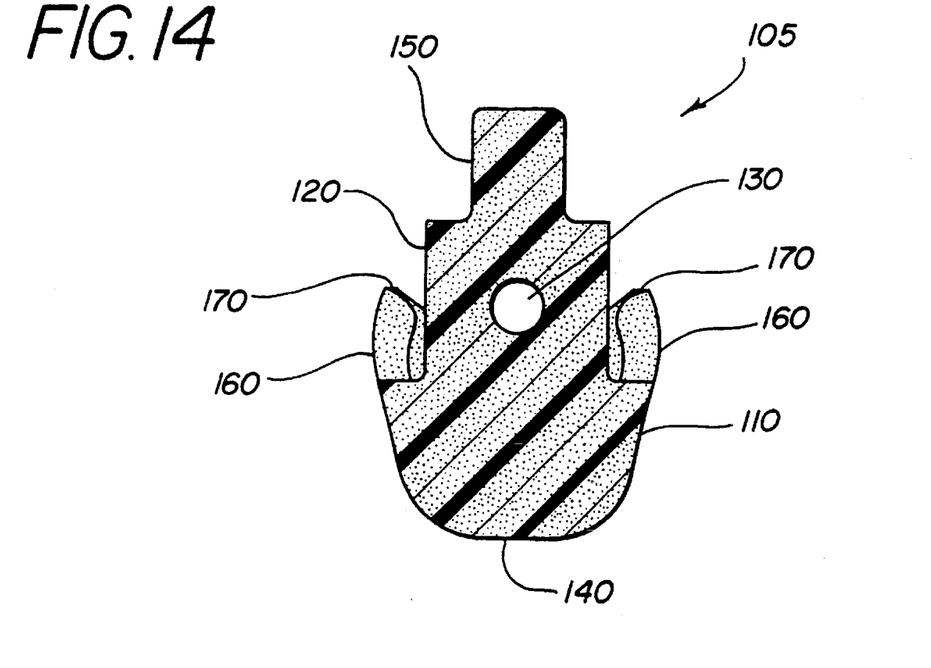
FIG. 14 is a cross-sectional view of the suture anchor of FIG. 10 taken along View Line 14—14.
Figure 15:
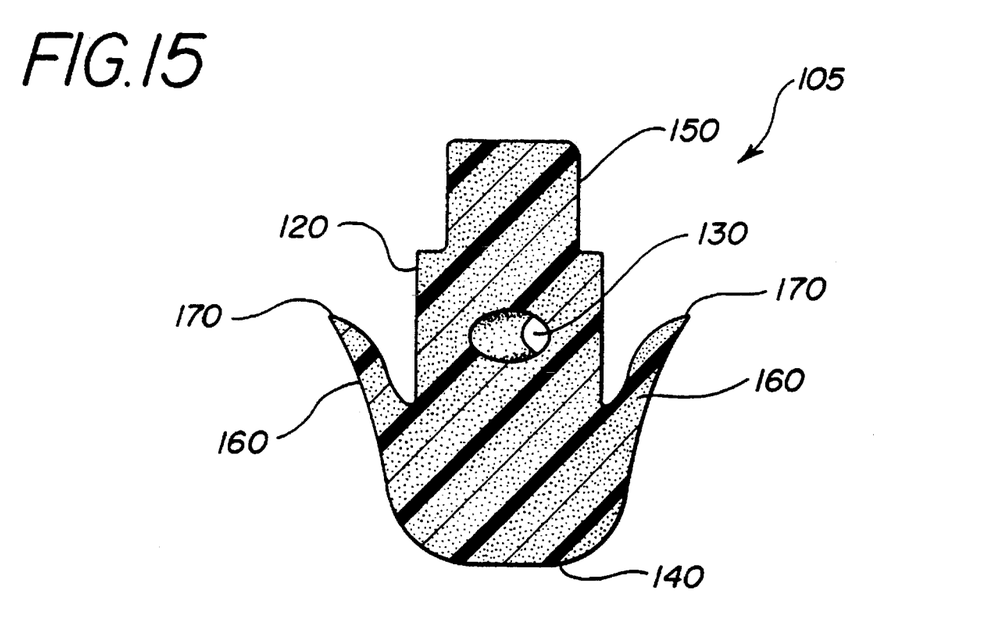
FIG. 15 is a cross-sectional view of the suture anchor of FIG. 10 taken a long View Line 15—15.

An applicator device 200 for inserting the suture anchors of the present invention is seen in FIG. 8. The applicator 200 is seen to have cylindrical housing 210 having a passage 212 therethrough. The cavity 220 is contained within housing 210. Cavity 220 is in communication with passage 212. Handle member 230 is seen to have shaft member 232 and top knob 234 mounted thereto. Shaft member 232 is slidably mounted in housing 210 in cavity 220. Shaft member 232 is seen to have passage 233 coaxial with passage 212. Detent member 214 is seen to extend into cavity 220 and into cavity 236 of shaft member 232 thereby providing a limit upon proximal and distal translation of shaft member 232 and shaft 260. Detent member 214 is preferably a screw although a pin or the like may be used. The spring member 238 is mounted in the distal section of cavity 220 and is seen to apply a proximal bias against shaft member 232. The tube 240 is seen to have proximal end 242, distal end 244 and passage 245 therethrough. The proximal end 242 of tube 240 is mounted in cavity 221 in the distal end 218 of housing 210. The passage 245 is in communication with passage 212. The shaft 260 is seen to have proximal end 262 and distal end 264. The shaft 260 is slidably mounted in housing 210 and tube 240. The proximal end 262 of shaft 240 is mounted to top knob 234 such that the shaft 260 can translate proximally or distally in passage 212. Mounted to the distal end 264 of shaft 260 is cylindrical member 270 having proximal end 273 and distal end 272. Extending from the distal end 272 of cylindrical member 270 are the distally extending, opposed spring members 274, which are biased to urge the spring members 274 apart. If desired, the spring members 274 may be mounted directly to shaft 260 using conventional mounting methods. Spring members 274 are seen to have opposed distal arcuate retention members 275 mounted to their distal ends. Retention members 275 are seen to have outer camming surfaces 276. In addition, each retention member 275 is seen to have a cavity 280 extending into the inner surface thereof which is configured to accept and engage, for example, a section of the shaft 20 and grasping member 50 of suture anchor 5 (see FIG. 8A). An alternate embodiment of the retention members 275 is seen in FIG. 8B wherein the cavities 280 are configured to only accept, for example, the grasping member 50. The spring members 274 are seen to be separated by gap 279 as are retention members 275. Preferably, the spring members 274 are biased radially outward. If desired, spring member 274 and retention member 275 may be formed as a unitary member, e.g., die-formed from a continuous piece of metal.

The apparatus 200 operates in the following manner. Initially, handle member 230 is depressed distally toward the distal end of cylindrical housing 210. This action pushes the shaft 260 distally, allowing the allowing the retention members 275 to open as they are moved distally, i.e., gap 279 increases. Using, for example, suture anchor 5, the shaft 20 and grasping member 50 of suture anchor 5 are then inserted into cavities 280 as shown in FIG. 8A. The spring biased handle member 230 is released causing the member 230 and shaft 260 to displace proximally. The camming surfaces 276 of retention members 275 engage the interior surface of the distal end 244 of shaft 240, thereby forcing the spring members 274 and retention members 275 toward each other, decreasing the gap 279 and causing the retention members 275 to effectively lock the shaft 20 and grasping member 50 of the suture anchor 5 tightly in cavities 280. The distal end of applicator 200 containing suture anchor 5 may then be inserted into the bore hole 315 as seen in FIGS. 7 or 16. Displacing handle member 230 distally releases the anchor 5 from retaining members 275.

While held in the grasp of applicator 200, the suture anchor 5 may be rotated in bore hole 315 by rotating the applicator 200. When suture anchor 5 is properly positioned below the cortical layer 305, the surgeon may release the anchor 5 by depressing handle member 230 distally causing the retention members 275 to move apart, which loosens the shaft 20 and grasping member 50 of the anchor 5 within cavities 280 sufficiently to effectively release anchor 5 from applicator 200.

The anchors of the present invention may be made from either conventional bioabsorbable materials or conventional non-absorbable materials, combinations thereof and equivalents thereof. Examples of absorbable materials include homopolymers and copolymers of lactide, glycolide, trimethylene carbonate, caprolactone, and p-dioxanone and blends or other combinations thereof and equivalent thereof. Of particular utility are the polylactides, especially poly[L(−)lactide], and the lactide-rich lactide/glycolide copolymers, especially 95/5 poly[L(−)lactide-co-glycolide].

Examples of non-absorbable materials from which the suture anchors of the present invention may be made include metallic biocompatible materials including stainless steel, Nitinol, titanium, Vitalium and equivalents thereof, polymeric materials such as non-absorbable polyesters, polyamides, polyolefins, polyurethanes, and polyacetals and equivalents thereof, and ceramic materials and equivalents thereof.

The suture anchor devices of the present invention, when made from an absorbable material, are preferably manufactured by molding using conventional injection molding equipment and conventional injection molding processes. A typical molding process includes the steps of (1) injecting a suitable polymer melt into an appropriately designed mold or cavity at process conditions conventionally employed for such polymer systems, (2) releasing from the mold, after the melt cools in the mold, polymer shaped in the proper configuration to meet the design criteria of the device. Additionally the anchor molded from the absorbable polymeric material, may be advantageously subjected to an annealing process to increase its mechanical or biological performance. Thermal annealing can also be used to increase the dimensional stability of molded parts by increasing the crystallinity levels in the parts. One or more surgical sutures, or one or more sutures with surgical needles attached, may be used in combination with the suture anchor and may be assembled prior to sterilization. The device can then be sterilized using conventional methods to render the anchor suitable for surgical applications.

The surgical needles 360 and sutures 350 which may be used with the suture anchors of the present invention include conventional sutures and conventional surgical needles and equivalents thereof. The sutures 350 may be absorbable or non-absorbable. The non-absorbable sutures 350 may be made from conventional materials including polyester, nylon, polypropylene, stainless steel, Vitalium alloy, Nitinol and the like and combinations thereof and equivalents thereof. The absorbable sutures 350 may be made from conventional materials such as poly(p-dioxanone), 95/5 poly [L(−)]lactide-co-glycolide]or combinations thereof and equivalents thereof.

The surgical needles 360 which may be used include conventional surgical needles such as stainless steel needles having conventional straight or curved configurations with conventional points such as taper points or cutting points or blunt points.

The suture anchor devices of the present invention have numerous advantages. The suture anchors of the present invention are very easy to manufacture. The anchor devices have stability when emplaced in bone and are easy to use. The suture anchors of the present invention do not simply rely on the friction between the device and the side walls of a hole drilled through bone to maintain their position within a bone, rather, they utilize a mechanical interference between the proximal edges of the wings and the inner surface of the bone cortex.

The suture anchor devices of the present invention can be used to reattach soft tissues to bone at various anatomical locations including the shoulder joint, hip joint, knee joint, etc., in either open or arthroscopic or endoscopic surgical procedures. The suture anchor devices, preferably when of a larger size, may also be used for fixation of bone fractures.

Example 1

A patient is prepared for surgery using conventional surgical preparatory techniques. The patient is anesthetized with a sufficient dose of a conventional anesthesia to induce an effective anesthetized state. An incision is made into to patient's knee joint in accordance with conventional surgical procedures and the end of the patient's femur adjacent to the knee joint is exposed. A bore hole is drilled into the patient's femur using a conventional drilling or boring instrument such as an orthopaedic drill. After the blind hole has been bored into the patient's femur and the bone surface has been cleaned of tissue debris, a surgical anchor device 5 of the present invention having a suture 350 and surgical needle 360 is inserted into the bore hole using an applicator 200 such that the proximal end 22 of the central shaft 20 and suture hole 30 are positioned below the outer surface of the cortex of the bone surrounding the bore hole. The proximal ends 64 of the wing members 60 are positioned below the inner-most surface of the cortex and are within the cancellous layer. The diameter of the bore hole is selected so that the wing members 60 of the anchor 5 are deflected sufficiently radially inward during insertion to effectively prevent the anchor 5 from moving within the bore hole. The deflection is a substantially elastic deformation. The anchor then is rotated sufficiently to effectively allow the cutting edges 70 on the sides 68 of each wing 60 to cut into the cancellous layer thereby enlarging the diameter of the bore hole in the proximity of the wing member 60 and allowing the wing member 60 to deflect radially outwardly. The anchor 5 is then released from the applicator 200. The wing members 60 now have a maximum outside diameter greater than the diameter of the bore hole. Therefore, a proximal force exerted upon the bone anchor is resisted by the wing members 60 digging into the cancellous layer and ultimately engaging the inner surface of the cortex thereby preventing the anchor 5 from being withdrawn from the bore hole. A tendon or ligament is then secured to the anchor 5 using the surgical needle 360 and suture 350. The incision in the patient's knee is then closed in accordance with conventional surgical procedures.

Example 2

A patient is prepared for arthroscopic shoulder surgery using conventional surgical preparatory techniques. The patient is anesthetized with a sufficient dose of a conventional anesthesia to induce an effective anesthetized state. Arthroscopic trocar cannulas are placed into the patient's shoulder in accordance with conventional arthroscopic techniques. An arthroscope is inserted through one cannula and upon examination a soft tissue lesion is identified. An appropriately sized hole is drilled into the patient's scapula, in the area of the glenoid rim, using a conventional boring instrument such as a drill bit or orthopaedic pin inserted through a trocar cannula. After the patient's scapula and the bone surface have been cleaned of tissue debris, a surgical anchor device 5 of the present invention having a suture 350 and surgical needle 360 is inserted through a trocar cannula and into the bore hole using an applicator 200 (the distal end of which is inserted into the trocar cannula) such that the proximal end 22 of the central shaft 20 and suture hole 30 are positioned below the outer surface of the cortex of the bone surrounding the bore hole. The proximal ends 64 of the wing members 60 are positioned below the inner-most surface of the cortex and are within the cancellous layer. The diameter of the bore hole is selected so that the wing members 60 of the anchor 5 are deflected sufficiently radially inward during insertion to effectively prevent the anchor 5 from moving within the bore hole. The deflection is a substantially elastic deformation. The anchor then is rotated sufficiently to effectively allow the cutting edges 70 on the sides 68 of each wing 60 to cut into the cancellous layer thereby enlarging the diameter of the bore hole in the proximity of the wing member 60 and allowing the wing member 60 to deflect radially outwardly. The anchor 5 is then released from the applicator 200 and the distal end of apparatus 200 is removed through the trocar cannula. The wing members 60 now have a maximum outside diameter greater than the diameter of the bore hole. Therefore, a proximal force exerted upon the bone anchor is resisted by the wing member 60 digging into the cancellous layer and ultimately engaging the inner surface of the cortex thereby preventing the anchor 5 from being withdrawn from the bore hole. A tendon or ligament is then secured to the anchor 5 using the surgical needle 360 and suture 350. The arthroscopic trocar cannulas are removed and the incisions in the patient's shoulder are then closed in accordance with conventional arthroscopic surgical procedures.

The suture anchors of the present invention and the applicator 200 may be used in a variety of surgical techniques including open procedures, arthroscopic procedures, laparoscopic procedures and endoscopic procedures.

Although this invention has been shown and described with respect to detailed embodiments thereof, it will be understood by those skilled in the art that various changes in form and detail thereof may be made without departing from the spirit and scope of the claimed invention.

What is claimed is:

1. A suture anchor device, comprising:
   an elongated anchor member having a distal end and a proximal end;
   a shaft extending proximally from the proximal end of the anchor member, said shaft having a distal end and a proximal end;
   a plurality of wing members extending proximally and radially outward from the proximal end of the anchor member, said members having a distal fixed end and a proximal free end and opposed longitudinally extending sides;
   cutting means along at least one side of at least one wing member; and,
   suture retaining means in said shaft; and
   wherein the distal end of the anchor member terminates in a blunted nose.

2. The device of claim 1 further comprising grasping means extending from the proximal end of the shaft.

3. The device of claim 1 further comprising a surgical suture mounted in the suture retaining means.

4. The device of claim 1 comprising longitudinally extending slots separating adjacent wing members.

5. The device of claim 1 wherein the device comprises a bioabsorbable material.

6. The device of claim 5 wherein the bioabsorbable material comprises a member selected from the group consisting of homopolymers and copolymers of lactide, glycolide, trimethylene carbonate, caprolactone, and p-dioxanone and blends thereof.

7. The device of claim 1 wherein the device comprises a biocompatible nonabsorbable material.

8. The device of claim 7 wherein the nonabsorbable material comprises a member selected from the group consisting of polyesters, polyamides, polyolefins, polyurethanes, and polyacetals.

9. The device of claim 1 wherein the suture retaining means is mounted in the shaft.

10. The device of claim 9 wherein the suture retaining means is in the proximal end of the shaft.

11. The device of claim 1 wherein the suture retaining means is mounted in the anchor member.

12. The device of claim 1 wherein the cutting means is provided by one side of at least one wing member having a greater thickness measured radially than the other side thereof.

13. The device of claim 12, wherein the cutting means additionally comprises an abrasive coating applied to the thicker side.

14. The device of claim 1 wherein the suture retaining means comprises a hole through the shaft.

15. The device of claim 1 wherein the suture retaining means comprises a hole through the anchor member.

16. The device of claim 1 wherein the wing members are resilient and, when deformed inwardly from their outwardly extending position, are biased to return to their pre-deformed shape.

17. A method of implanting a suture anchor device in a bone, comprising:
   I) inserting a suture anchor device in a bore hole drilled in a bone, wherein the suture anchor device comprises:
   an elongated anchor member having a distal end and a proximal end;
   a shaft extending proximally from the proximal end of the anchor member, said shaft having a distal end and a proximal end;
   a plurality of wing members extending proximally and radially outward from the proximal end of the anchor member, said members having a distal fixed end and a proximal free end and opposed longitudinally extending sides;
   cutting means along at least one side of at least one wing member; and,
   suture retaining means in said shaft; and
   II) rotating the suture anchor device sufficiently to effectively anchor the suture anchor device in the bore hole by enlarging the diameter of at least part of the bore hole below the surface of the bone through the cutting action of the cutting means as the suture anchor device is rotated.

\* \* \* \* \*